US011199526B2

(12) United States Patent
Lachine et al.

(10) Patent No.: US 11,199,526 B2
(45) Date of Patent: Dec. 14, 2021

(54) DETERMINING HYDROCARBON CONTENT IN STEAM CONDENSATE

(71) Applicant: ExxonMobil Research and Engineering Company, Annandale, NJ (US)

(72) Inventors: Randall S. Lachine, Brights Grove (CA); Raymond J. Henry, Calgary (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 118 days.

(21) Appl. No.: 16/218,785

(22) Filed: Dec. 13, 2018

(65) Prior Publication Data

US 2019/0187121 A1 Jun. 20, 2019

Related U.S. Application Data

(60) Provisional application No. 62/607,471, filed on Dec. 19, 2017.

(51) Int. Cl.
*G01N 30/06* (2006.01)
*G01N 33/18* (2006.01)
(Continued)

(52) U.S. Cl.
CPC ......... *G01N 30/06* (2013.01); *G01N 33/1833* (2013.01); *G01N 2030/025* (2013.01);
(Continued)

(58) Field of Classification Search
CPC ............. G01N 30/06; G01N 2030/025; G01N 2030/062; G01N 2030/065; G01N 33/1833; G01N 2030/8854
See application file for complete search history.

(56) References Cited

U.S. PATENT DOCUMENTS 3,418,841 A 12/1968 Issenmann
4,943,161 A * 7/1990 Michaelis .......... G01N 33/1833
356/437

(Continued)

FOREIGN PATENT DOCUMENTS

PL 214183 B1 6/2013

OTHER PUBLICATIONS

Oram, "Disinfection By-Products Trihalomethanes", as downloaded from the Internet Archive on Nov. 1, 2016.*

(Continued)

*Primary Examiner* — Justin N Olamit
(74) *Attorney, Agent, or Firm* — Glenn T. Barrett

(57) ABSTRACT

Systems and methods are provided for determining a content of a hydrocarbon or other compound, such as a $C_3$ to $C_7$ hydrocarbon, in a condensed steam sample. Cooled steam condensate can be flowed through a sample chamber including an inner overflow tube. When the flow stops, water can be drained from the sample chamber, and then the sample chamber can be opened to allow fluid communication with a vapor chamber above the sample chamber. This can allow hydrocarbons in the condensed steam (and/or other gas) to be transferred from the sample chamber into the vapor chamber. The vapor chamber can then be isolated from the sample chamber. At least a portion of the content of the vapor chamber can then be passed to a detection volume, such as the characterization cell for a gas chromatography system.

14 Claims, 6 Drawing Sheets

(51) Int. Cl.
  *G01N 30/88*  (2006.01)
  *G01N 30/02*  (2006.01)

(52) U.S. Cl.
  CPC .................. *G01N 2030/065* (2013.01); *G01N 2030/8854* (2013.01)

(56) References Cited

U.S. PATENT DOCUMENTS

| | | | |
|---|---|---|---|
| 5,447,052 A | | 9/1995 | Delaune et al. |
| 5,889,202 A | | 3/1999 | Alapati et al. |
| 6,392,115 B1 | * | 5/2002 | Gasem ...................... C07C 7/08 585/807 |
| 2013/0071867 A1 | | 3/2013 | Fadgen |
| 2018/0136187 A1 | * | 5/2018 | Doutt ..................... G01N 30/30 |
| 2018/0284088 A1 | * | 10/2018 | Verbeck, IV ...... G01N 33/0036 |

OTHER PUBLICATIONS

The International Search Report and Written Opinion of PCT/US2018/065365 dated Mar. 26, 2019.

\* cited by examiner

DETERMINING HYDROCARBON CONTENT IN STEAM CONDENSATE

CROSS-REFERENCE TO RELATED APPLICATIONS

This application claims priority to U.S. Provisional Application Ser. No. 62/607,471 filed Dec. 19, 2017, which is herein incorporated by reference in its entirety.

FIELD OF THE INVENTION

The invention relates to detecting hydrocarbons in steam condensate, such as detection of hydrocarbons in steam used in a heat exchanger.

BACKGROUND OF THE INVENTION

Steam is commonly used as the heat transfer fluid in various types of heat exchangers in petroleum production and/or processing environments. In many circumstances, the heat exchangers are designed to be in direct contact with one or more fluids in the processing environment. This typically involves bringing steam at a higher (lower) temperature into the heat exchanger via one or more pipes from outside of the processing environment, performing heat exchange, and then withdrawing the colder (hotter) steam using one or more additional pipes.

In order to pass the steam into the heat exchanger, a seal between the heat exchanger and the pipe delivering steam to the heat exchanger will typically be present at some location. A similar seal can be present between the heat exchanger and the exit pipe. In order to keep both process fluids and the steam contained within reactor shells, these seals may also be exposed to the process fluids in the processing environment. If some type of seal failure or breakdown occurs, the process fluids in the processing environment can potentially enter the heat exchanger/steam transport system, resulting in contamination of the steam with a hydrocarbon or other process fluid. The likelihood of such contamination can be increased if the pressure in the processing environment is greater than the pressure within the heat exchanger. Similarly, if the heat exchanger bundles themselves develop a crack or leak, the process fluids in the processing environment can potentially enter the heat exchanger/steam transport system.

An example of a processing environment where steam is used as the heat transfer fluid in a heat exchanger is pentane recovery system as part of processing of oil sands. During processing of oil sands, a paraffinic froth treatment can be used to separate a desired bitumen product from at least a portion of the particulates and water in the bitumen. Pentane can be a suitable solvent to use for the paraffinic froth treatment, either in the form of a single component such as n-pentane, or in the form of a mixture of $C_5$ hydrocarbons, such as a mixture of n-pentane and isopentane. After using the pentane to separate the bitumen-containing froth from water, particulates, and/or other components that are not soluble in the solvent, one or more solvent recovery steps can be used to recover the pentane from the bitumen. In many of these solvent recovery steps, the goal of the process can be to vaporize the hydrocarbon solvent (such as pentane) to separate it from the bitumen product while reducing or minimizing the amount of bitumen entrained with the vaporized solvent. This can potentially involve, for example, separations performed at elevated temperatures and/or pressures. During these solvent recovery steps, heat exchangers may be used to manage the temperature. For solvent recovery steps performed in a processing environment at pressures greater than 100 kPa-a, steam can be a suitable heat transfer fluid, although the pressure within the heat exchanger may be lower than the pressure in the processing environment. In this type of situation, the hydrocarbon vapor (such as pentane vapor) from the processing environment can potentially enter into the heat exchanger/steam transport system if any material failures are present.

When some type of material failure occurs in a heat exchanger, it can be beneficial to identify the failure at an early stage. In a petroleum processing or production environment, one method for detecting such a material failure can be based on detecting the presence of a hydrocarbon contaminant within the steam used as the heat transfer fluid. Unfortunately, conventional methods for detecting hydrocarbon contaminants in steam from a heat exchanger system suffer from a variety of difficulties.

One conventional option for detecting the presence of hydrocarbons in steam can be to use a gas sparging system. After condensing the steam to form liquid water, a gas sparging system can finely disperse air into the liquid water stream to remove lower boiling components, such as pentane. However, gas spargers are prone to fouling, in part due to the small opening size of the gas outlets in the sparger. This susceptibility to fouling can result in the need for frequent cleaning. In addition to requiring taking the system off-line, the cleaning itself can also present problems, as typical gas spargers can be constructed of components that are susceptible to breaking when handled.

Another conventional option can be to attempt to detect the hydrocarbons with ultraviolent spectroscopy. Unfortunately, the typical adsorption wavelengths used for detection of hydrocarbons can overlap with adsorption wavelengths for other types of contaminants. This can make it difficult to distinguish between situations where a material failure has occurred in the heat exchanger system versus situations where other (possibly acceptable) contaminants are present within the steam.

What is needed are systems and methods for identifying hydrocarbon contamination within a heat exchanger system (or other system involving transport of steam) while reducing or minimizing maintenance requirements, measurement variability, and/or detection difficulties.

SUMMARY OF THE INVENTION

In various aspects, a method for characterizing hydrocarbon content in steam condensate is provided. The method can include flowing water comprising condensed steam and at least one hydrocarbon at a first temperature through a sample chamber comprising an inner overflow tube, such as a vertically-oriented sample chamber comprising an inner overflow tube. The flow of water can correspond to, for example, condensed steam from a heat exchanger system. The inner overflow tube can define an annular volume between the inner overflow tube and an interior surface of the sample chamber. The flow of water into the sample chamber can then be stopped. Prior to, during, and/or after the flowing of the water, the sample chamber can be heated to a second temperature of 40° C. to 90° C. Gas comprising the at least one hydrocarbon can then be transferred from the sample chamber into a vapor chamber. Optionally, the vapor chamber can also be heated to the second temperature prior to and/or during the transferring. The vapor chamber can then be isolated from the sample chamber. After isolation, at least a portion of the transferred gas from the vapor chamber can be passed into a detection volume. A hydrocarbon content in the detection volume can then be characterized via gas chromatography. For example, a pentane content in the condensed steam can be determined based on a pentane and/or isopentane content that is characterized in the detection volume. In other examples, the hydrocarbon content can correspond to a content of one or more $C_3$-$C_7$ hydrocarbons.

In some aspects, the method can further include draining water from the sample chamber via the inner overflow tube after stopping the flow of water into the sample chamber.

Prior to stopping the flow, the water level in the sample chamber can optionally be above a top surface of the inner overflow tube. The draining can optionally further include opening a vent in the sample chamber during the draining.

In some aspects, characterizing the hydrocarbon content in the detection volume can correspond to determining an amount of hydrocarbon content using a thermal conductivity detector. For example, a thermal conductivity of the at least a portion of the transferred gas in the detection volume can be compared with a thermal conductivity of a reference flow in a reference volume.

In some aspects, the first temperature can be 5° C. to 50° C. This can optionally correspond to a temperature below the boiling point of the at least one hydrocarbon. Additionally or alternately, the second temperature can greater than the first temperature by at least 10° C.

In some aspects, the method can further include pressurizing the vapor chamber to a pressure of 50 kPa-g or more after isolating the vapor chamber and prior to passing the at least a portion of the transferred gas into the detection volume. The pressurizing can be performed using a convenient inert gas, such as $N_2$.

In various aspects, a system for characterizing a hydrocarbon content in steam condensate (such as steam condensate from a heat exchanger) is also provided. The system can include a sample chamber comprising a sample inlet, an overflow tube, an overflow tube outlet, and a sample outlet. The sample inlet can be in selective fluid communication with a source of water comprising condensed steam. The sample chamber can optionally further comprising a sample vent. The system can further include a heater associated with the sample chamber. The system can further include a vapor chamber in selective fluid communication with the sample outlet via at least a first valve. The system can further include a detection volume in selective fluid communication with the vapor chamber via at least a second valve. The system can further include a gas chromatograph associated with the detection volume for characterizing a hydrocarbon content in the detection volume.

In some aspects, the gas chromatograph can include a thermal conductivity detector associated with the detection volume. Additionally or alternately, the detection volume can include a chromatography column.

In some aspects, the system can further include a gas source in selective fluid communication with the vapor chamber via at least a third valve, such as a source of $N_2$.

In some aspects, the system and methods described herein can be more generally used to characterize compounds other than hydrocarbons, such as hydrocarbon-like compounds and/or compounds having a boiling point of 100° C. or less, or 95° C. or less, at 100 kPa-a.

DETAILED DESCRIPTION

Figure 1:
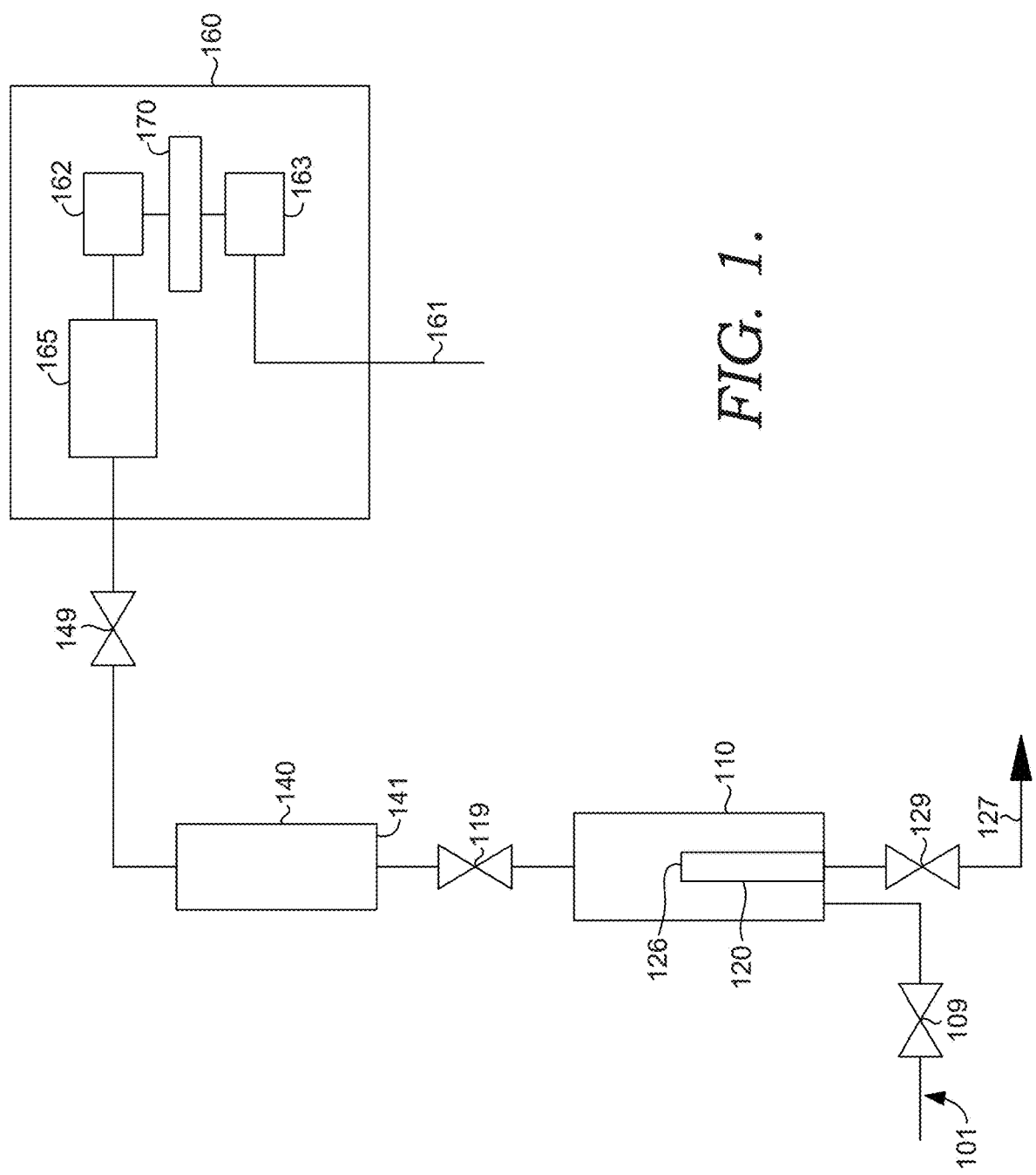
FIG. 1 shows a sample configuration for determining hydrocarbon content in a condensed steam sample.

All numerical values within the detailed description and the claims herein are modified by "about" or "approximately" the indicated value, and take into account experimental error and variations that would be expected by a person having ordinary skill in the art.

In various aspects, systems and methods are provided for determining a content of a small hydrocarbon, such as a $C_3$ to $C_7$ hydrocarbon, and/or other types of compounds in a condensed steam sample. Cooled steam condensate can be flowed through a sample chamber including an inner overflow tube. The inner overflow tube defines an annular volume between the tube and an interior surface of the sample chamber. When the flow stops, any excess water above the level of the overflow tube can be drained from the sample chamber. Preferably, the flow rate of water into the sample volume can be low enough that water can be drained away via the overflow tube without allowing the level of the water to rise substantially above the top surface of the overflow tube. This can leave behind a substantially constant amount of water in the annular volume. Prior to, during or after the flowing of water (condensed steam) into the sample chamber, the sample chamber and/or the contents of the sample chamber can be heated to a temperature between 40° C. and 90° C., such as 60° C. to 80° C. For example, the sample chamber can be heated to a desired temperature prior to flowing the condensed steam through the sample chamber. This can allow the sample chamber to be maintained at a relatively constant temperature. After the flow of condensed steam into the sample chamber is stopped, the water remaining in the sample chamber after draining can be heated toward the temperature of the sample chamber. In some aspects, the water can be held in the sample chamber for a period of time that allows for heating of the water in the sample chamber to a desired temperature, such as a temperature greater than the boiling point of the hydrocarbon that is being characterized. This can drive any hydrocarbons that are solvated in the condensed steam into the gas phase. The sample chamber can then be opened to allow fluid communication with a vapor chamber above the sample chamber. This can allow hydrocarbons in the condensed steam (and/or other gas) to be transferred from the sample chamber into the vapor chamber. The fluid communication can be maintained for a sufficient period of time to allow for reproducible characterization of an amount of hydrocarbon. After the period of time, the vapor chamber can be isolated from the sample chamber. The vapor chamber can then optionally be pressurized to a desired pressure. The content of the vapor chamber can then be passed to a detection volume, such as the characterization cell for a gas chromatography system. In some aspects, the gas chromatography system can include a reference volume so that a thermal conductivity detector can be used to determine an amount of hydrocarbon in the content of the vapor chamber. In such a configuration, the sample can be eluted through a gas chromatography apparatus, followed by passing through the thermal conductivity detector to determine the amount of any contaminants not present in the reference sample.

In various embodiments, use of a sample chamber, a vapor chamber, and a detection volume associated with a gas chromatograph can provide one or more advantages when characterizing hydrocarbon content in a condensed steam sample. The system including the sample chamber, vapor chamber, and detection volume associated with a gas chromatograph does not include any orifices or chambers that are prone to plugging, in contrast to a gas sparging system. This can allow the system to be operated for desirable run length between maintenance and/or shutdown events. Additionally or alternately, by using a system that ultimately allows for characterization of a sample using gas chromatography, a hydrocarbon or hydrocarbons of interest in the sample can be characterized while reducing or minimizing the potential for other contaminants to interfere with the characterization.

In various aspects, the systems and methods described herein can also be beneficial for providing a reproducible method of characterizing hydrocarbon content in a condensed stea sample. Using a sample chamber with an inner overflow tube can allow a substantially consistent or repeatable amount of water to be collected in the sample chamber. This can facilitate comparison between various measurements. Further consistency between measurements can potentially be achieved by using a vapor chamber to transfer a substantially consistent or repeatable amount of gas from the sample chamber to the vapor chamber. Additionally, the transfer time can be sufficiently long relative to the temperature during the transfer so that the transferred vapor is substantially in equilibrium with the liquid in the sample chamber. The use of gas chromatography in conjunction with a thermal conductivity detector can then allow for sufficient sensitivity to determine the concentration of the hydrocarbon in the sample, as well as distinguishing between different types of hydrocarbons. Based on the repeatable nature of the system and method, the conductivity difference between the sample derived from the condensed steam and the reference sample can be used to determine a quantitative amount of hydrocarbon present in the condensed steam.

When characterization of steam from a system is desired, a portion of the steam from the system can be withdrawn, condensed, and passed through the sample volume. After cooling the steam sufficiently to from liquid water, the condensed water can be further cooled to a desired first temperature prior to entering the sample chamber. The first temperature can correspond to any convenient temperature between 1° C. and 50° C. In some aspects, the first temperature can be less than the boiling point temperature for the hydrocarbon contaminant(s) that are being detected. In some aspects, the first temperature can be 10° C. to 30° C., or 15° C. to 25° C. The cooling of the portion of the steam to form a condensed steam (water) flow at a desired temperature can be performed by any convenient method, such as by heat exchange and/or radiative cooling.

The flow based on the condensed steam can then be passed into a sample chamber that includes an inner overflow tube. The sample chamber can correspond to a chamber having any convenient total volume. Some of this volume can be occupied by the inner overflow tube. A portion of the volume can be above the level of the top of the inner overflow tube (relative to the direction of gravitational force). Another portion of the remaining volume can correspond to a substantially annular volume. In some aspects, the sample chamber can be oriented in a substantially vertical manner, so that the input flow of condensed steam enters the sample chamber from below the level of the top of the inner overflow tube.

As the condensed steam flows into the sample chamber, the level of water in the sample chamber will rise until it is at the level of the top of the inner overflow tube. At that point, water will start to drain from the sample chamber via the inner overflow tube. When desired, the flow into the sample chamber can be stopped, such as by such as by closing a valve in the flow path for delivering condensed steam to the sample chamber. For example, the flow of condensed steam into the sample chamber can be maintained for a period of time, such as 1 minute to 5 minutes, or 2 minutes to 4 minutes, to allow excess water to be introduced into the sample chamber that is greater than the annular volume below the top of the inner overflow tube. Any water in the sample chamber above the level of the inner overflow tube can then drain out, leaving behind an amount of condensed steam in the substantially annular volume. By draining via the inner overflow tube, a substantially constant amount of water can be retained in the sample chamber after the draining.

It is noted that after the valve is closed to stop the flow of condensed steam into the sample chamber, a vent can be opened in the sample chamber to allow the pressure in the sample chamber to stay near ambient while any excess water is drained via the inner overflow tube. Alternatively, if desired, an additional stream of low pressure nitrogen can be made available to allow the sample chamber to maintain a desired pressure during draining of water via the inner overflow tube. This additional nitrogen source can be stopped after draining is completed.

In some alternative aspects, a valve in the inner overflow tube flow path can be closed initially. In such aspects, the sample chamber can be filled to a desired level and the flow can be stopped, such as by closing a valve in the flow path for delivering condensed steam to the sample chamber. In such aspects, the flow path for the inner overflow tube can then be opened to allow water to drain from the sample tube until the water level falls below the top of the inner overflow tube.

After draining from the inner overflow tube is completed, the flow path for the inner overflow tube can be closed, such as by closing a valve. A flow path can then be opened between the sample chamber and a vapor chamber. It is noted that the flow path between the sample chamber and vapor chamber can generally be closed, except for during the time period when transfer of gas is desired between the sample chamber and the vapor chamber. Before opening the flow path to the vapor chamber, the vapor chamber can optionally be purged with an inert gas, such as nitrogen, and then optionally pumped out to reduce the pressure in the vapor chamber. For example, the pressure in the vapor chamber can be reduced to 90 kPa-a or less, or 80 kPa-a or less. Optionally, the flow path between the vapor chamber and the sample chamber can be at least partially evacuated prior to opening the flow path. In some aspects, the vapor chamber can be located above the level of the sample chamber, to assist with the transfer of gas from the sample chamber to the vapor chamber.

Prior to, during, and/or after opening the flow path between the sample chamber and the vapor chamber, the temperature of the condensed steam (water) in the sample chamber and the vapor chamber can be heated (increased) to a second temperature. Additionally or alternately, the sample chamber and vapor chamber can be heated to and/or maintained at the second temperature. For example, it may be desirable to maintain the sample chamber and the vapor chamber at the second temperature. When the flow into the sample chamber is stopped and excess water is drained, the remaining water in the sample chamber can begin to heat based on the higher temperature being maintained for the sample chamber. In such aspects, the water can optionally be held in the sample chamber for a period of time prior to opening the valve between the sample chamber and the vapor chamber, so that the temperature of the water in the sample chamber can be increased. For example, the water can be held in the sample chamber for 1 minute to 30 minutes (or 1 minute to 10 minutes) prior to allowing fluid communication between the sample chamber and the vapor chamber. It is noted that the temperature of the contents of the sample chamber may be lower than the sample chamber itself during the transfer of gas between the sample chamber and the vapor chamber. In such an aspect, the temperature of the contents of the sample chamber may continue to increase during the transfer of gas to the vapor chamber. Heating the water can assist with driving gas solvated in the condensed steam into the gas phase. The second temperature can correspond to any convenient temperature between 40° C. and 90° C. In some aspects, the second temperature can be at least 10° C. greater than the first temperature, or at least 20° C. greater. In some aspects, such as aspects where the temperature of the sample chamber is controlled, the second temperature can be at least 20° C. greater than the boiling point of the hydrocarbon being characterized, or at least 30° C. greater. In such aspects, even though the temperature of the water in the sample chamber may be lower than the sample chamber itself, the heating of the water toward the temperature of the sample chamber can be sufficient to allow the temperature of the water to be greater than the boiling point of the hydrocarbons in the water. In some aspects, the first temperature can be 40° C. to 90° C., or 50° C. to 70° C., or 60° C. to 80° C., or or 70° C. to 90° C. The heating of the water in the sample chamber to the second temperature can be performed by any convenient method, such as by heat exchange and/or using a heater.

The fluid communication between the sample chamber and the vapor chamber can be maintained for a period of time. The period of time can be any convenient period of time that roughly allows for equilibration between the sample chamber and the vapor chamber at the second temperature. In aspects where the condensed steam sample is held in the sample chamber for a period of time prior to opening the valve between the sample chamber and the vapor chamber, the time period for maintaining fluid communication between the sample chamber and the vapor chamber can potentially be shorter, as a substantial portion of the hydrocarbons from the condensed steam may already be in the gas phase prior to starting the transfer of gas between the sample chamber and the vapor chamber. In other aspects where there is only a short delay between the end of draining the sample chamber and opening the isolation valve between the sample chamber and the vapor chamber, the period of time for allowing fluid communication between the sample chamber and the vapor chamber can be 1 minute to 30 minues, or 10 minutes to 30 minutes. This can provide sufficient time for hydrocarbon that is initially solvated in the condensed steam in the sample chamber to become gas phase hydrocarbon, which can then be distributed uniformly between the gas phase volume in the sample chamber plus vapor chamber (plus any flow path between the chambers).

After the period of time for equilibration between the sample chamber and the vapor chamber, the flow path between the sample chamber and the vapor chamber can be closed, such as by closing a valve. At this point, the pressure in the vapor chamber may be near ambient or slightly below ambient. Optionally, additional gas can be added to the vapor chamber to increase the pressure in the vapor chamber. For example, additional $N_2$ can be added to the vapor chamber to increase the pressure in the vapor chamber to a pressure of 50 kPa-g or more, or 70 kPa-g or more, or 90 kPa-g or more. A flow path between the vapor chamber and a detection volume for a gas chromatograph can then be opened (such as by opening a valve). In this discussion, the detection volume for a gas chromatograph can refer a sample cell, a chamber, a chromatography column, and/or any other volume typically used as part of characterization of a sample using a gas chromatograph. Opening the flow path between the vapor chamber and the detection volume can allow the gas in the vapor chamber to be passed into the detection volume for characterization by gas chromatography. Any convenient gas can be used as the carrier gas for the gas chromatography, such as helium.

In some aspects, the characterization by gas chromatography can include characterization using a thermal conductivity detector. In such aspects, after passing a portion of the gas from the vapor chamber through the column, the output from the column can be passed through a cell associated with thermal conductivity detection. A second parallel cell can also be used that contains a reference flow. The conductivity of the flows in the two cells can be compared to determine a concentration of components that are different between the detection cell and the reference cell.

The above methodology can allow for preparation of a sample for characterization by gas chromatography (optionally including a thermal conductivity detector) in a manner that facilitates comparison between samples. In particular, that above methodology can allow a) a substantially constant amount of condensed steam when gathering a sample in the annular volume of the sample chamber; b) transfer of a gas phase from the sample chamber to the vapor chamber under substantially constant conditions; and c) characterization of the vapor in the vapor chamber using a method suitable for making comparisons between samples.

In some aspects, the system and methods described herein can be used for characterization of small hydrocarbons, such as $C_3$ hydrocarbons (e.g., propane) to $C_7$ hydrocarbons (e.g., heptane). More generally, any hydrocarbon or hydrocarbon-like compound with a boiling point lower than the boiling point of water can potentially be characterized using the methods described herein. Still more generally, any compound in water that evaporates in a boiling range below the boiling point of water can potentially be suitable for characterization (i.e., a compound with a boiling point of less than 100° C. at a pressure of ~100 kPa-a, or less than 95° C.). A hydrocarbon-like compound refers to a compound that includes carbon, hydrogen, and one or more heteroatoms different from carbon or hydrogen. Preferably, if a hydrocarbon-like compound is characterized by the following methods, the hydrocarbon-like compound can correspond to a compound that does not remain at least partially in an aqueous solution after being to heated above the boiling point of the hydrocarbon-like compound. Ethanol is an example of a hydrocarbon-like compound that remains in aqueous solution after being heated to greater than the boiling point of ethanol.

Examples of Configurations for Hydrocarbon Characterization

FIG. 1 schematically shows an example of a configuration for determining the hydrocarbon content of a condensed steam sample (i.e., a water sample). In FIG. 1, a stream of condensed steam 101 that may contain one or more hydrocarbon contaminants is passed through valve 109 that provides selective fluid communication between the source of condensed steam 101 and sample chamber 110. The condensed steam 101 can be condensed steam at a first temperature. The fluid communication is defined as selective based on the ability to open or close valve 109, which can allow fluid communication (open) or prevent fluid communication (closed). When a sufficient amount of condensed steam is passed into the sample chamber 110, the liquid level of the condensed steam can be at the level of the top surface 126 of inner overflow tube 120 (or optionally above the level of top surface 126). Water entering the inner overflow tube 120 can exit from the system via overflow drain 127. Optionally, overflow drain 127 can feed into a common drain system.

After a period of time, valve 109 can be closed. Any remaining water at or above the top 126 of the inner overflow tube 120 can then exit from the sample chamber 110 via drain 127. It is noted that sample chamber 110 can include a vent (not shown) that can be opened when attempting to drain water from the sample chamber 110 via drain 127. After draining is completed (such as after a draining time period or after detection of a water level below the top of the inner overflow tube), drain valve 129 can be closed, along with any optional vents that were opened to facilitate draining. Prior to, during, and/or after the closing of valves 109 and 129, the vapor chamber 140 can optionally be purged with nitrogen 141 (or another inert gas stream) and/or partially evacuated to reduce the pressure in the vapor chamber 140. Valve 119 can then be opened to allow gas to transfer from sample chamber 110 to vapor chamber 140. Thus, sample chamber 110 and vapor chamber 140 are in selective fluid communication via valve 119. Prior to, during, and/or after opening valve 119, the sample chamber 110 and vapor chamber 140, and/or the gas in sample chamber 110 and the gas in vapor chamber 140, can be heated (not shown) to a second temperature that is higher than the first temperature. This can facilitate causing hydrocarbons solvated in the liquid water in sample chamber 110 to become gas phase hydrocarbons. The transfer of gas between sample chamber 110 and vapor chamber 140 can continue for a period of time at the second temperature. After the period of time, valve 119 can be closed.

After closing valve 119, vapor chamber 140 can optionally be pressurized using nitrogen 141. After optional pressurization, valve 149 can then be opened to allow gas from vapor chamber 140 to pass into gas chromatograph system 160. For example, gas from vapor chamber 140 can pass into the separation column 165 of gas chromatograph 160. The separation column 165 corresponds to a detection volume for gas chromatograph 160. Thus, vapor chamber 140 is in selective fluid communication with a detection volume (separation column 165) via valve 149. After passing through separation column 165, the flow from separation column 165 can be passed into a flow cell 162 for a thermal conductivity detector 170. A reference flow 161 can also be passed through reference flow cell 163 to allow for characterization by thermal conductivity detector 170 of the hydrocarbon content passing through flow cell 162.

Figure 2:
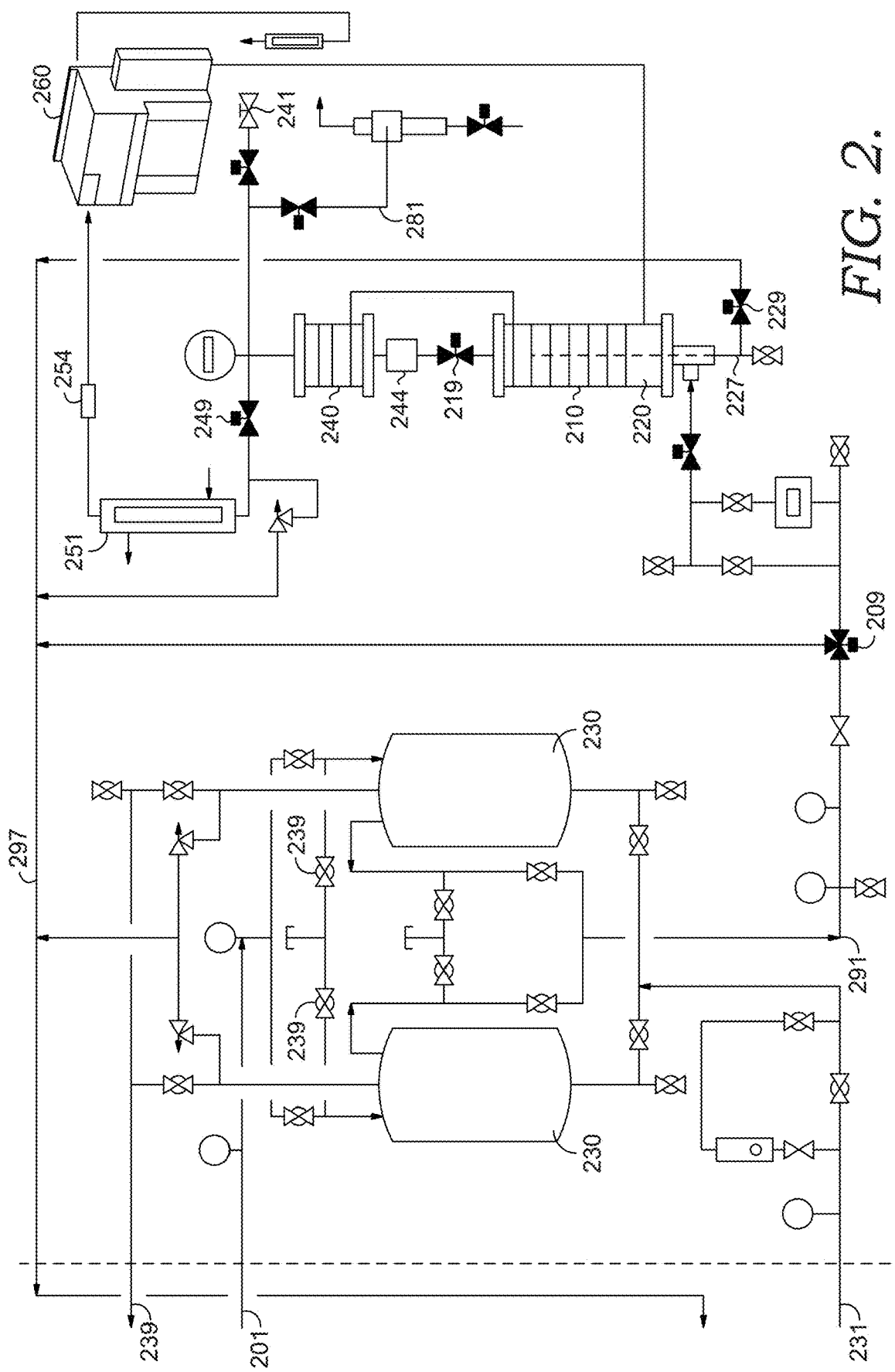
FIG. 2 shows another sample configuration for determining hydrocarbon content in a condensed steam sample.
Figure 3:
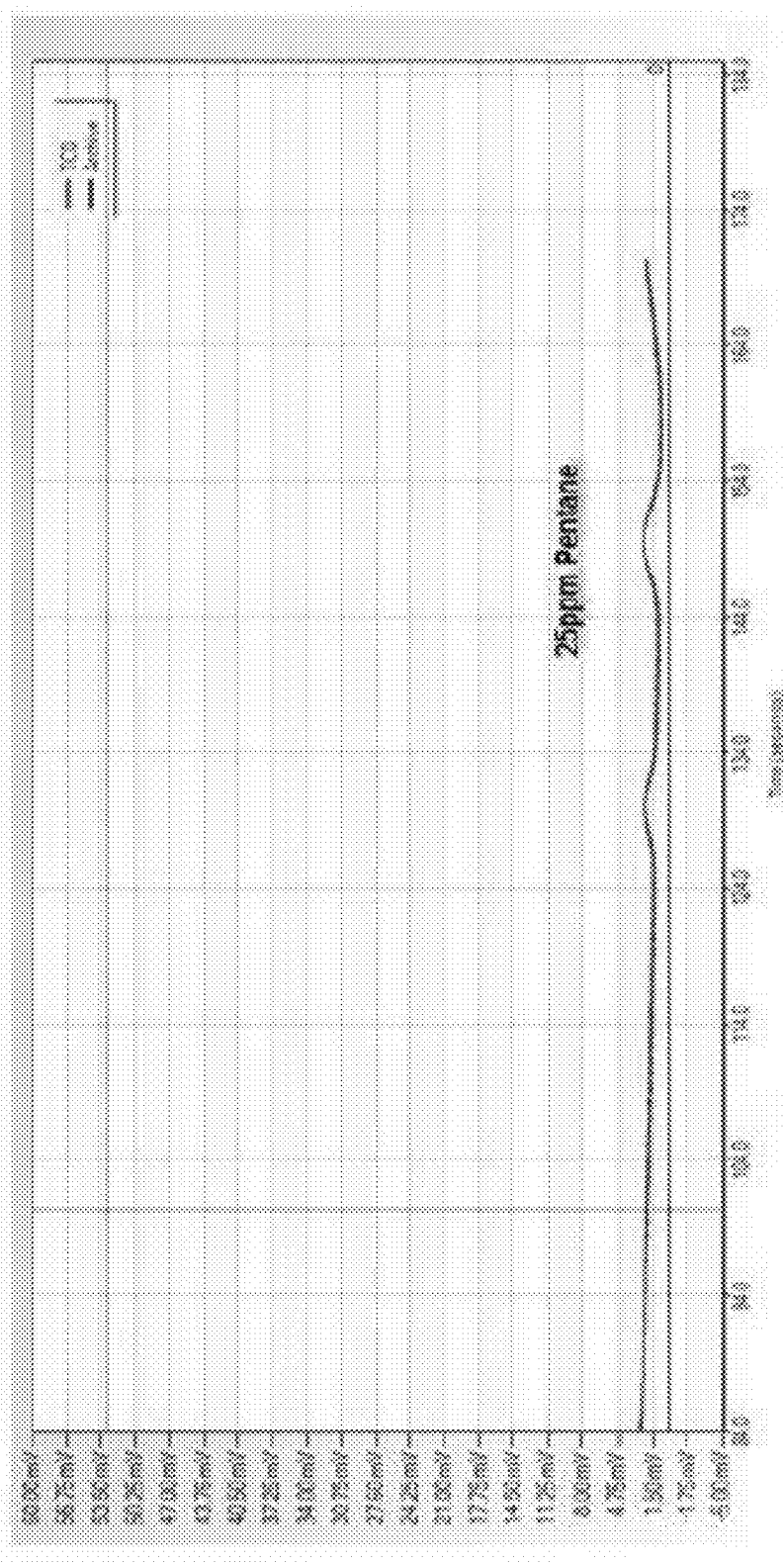
FIG. 3 shows a gas chromatography/thermal conductivity detector characterization of pentane in water using a system and method according to an embodiment of the invention.
Figure 4:
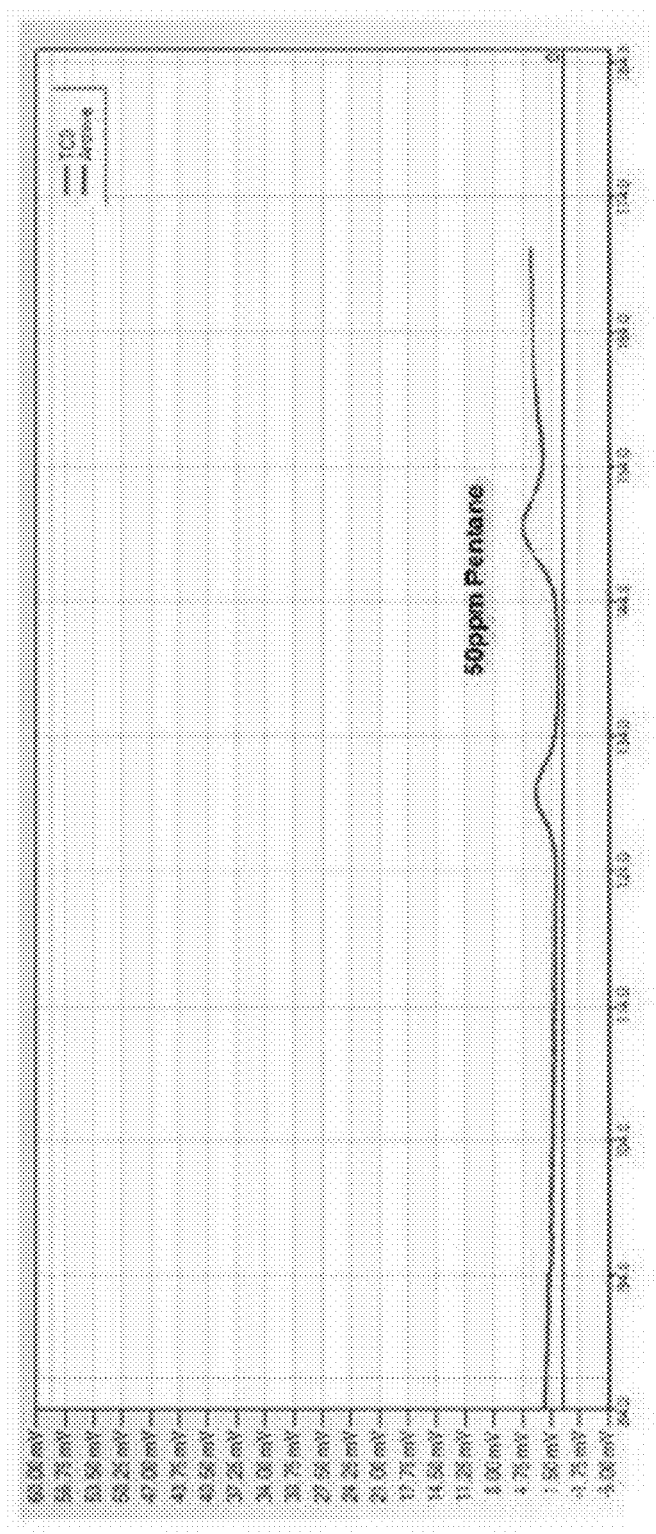
FIG. 4 shows a gas chromatography/thermal conductivity detector characterization of pentane in water using a system and method according to an embodiment of the invention.
Figure 5:
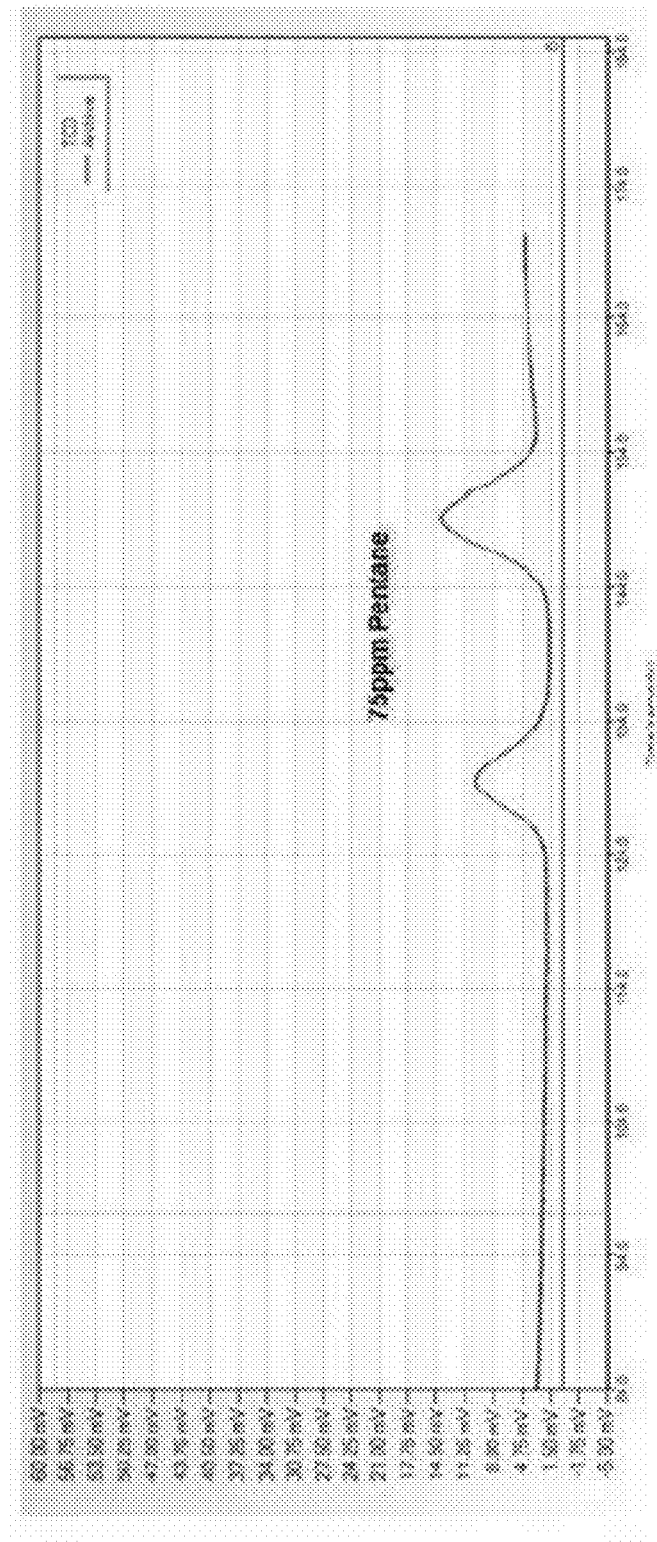
FIG. 5 shows a gas chromatography/thermal conductivity detector characterization of pentane in water using a system and method according to an embodiment of the invention.
Figure 6:
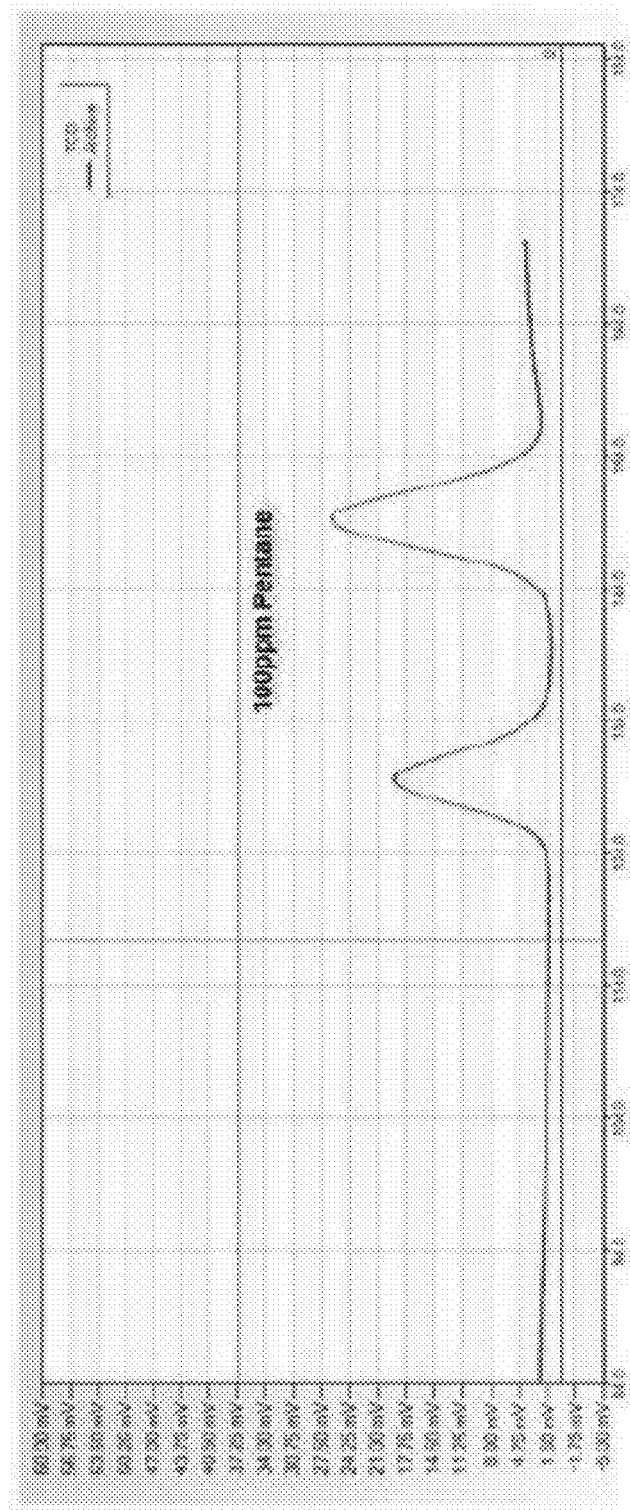
FIG. 6 shows a gas chromatography/thermal conductivity detector characterization of pentane in water using a system and method according to an embodiment of the invention.

While FIG. 1 provides an overview of operation of a system for characterizing the hydrocarbon content of condensed steam, many additional pipes, valves, heating and cooling elements, and other potential components could be present in such a system. FIG. 2 shows an example of a system for characterizing the hydrocarbon content of condensed steam at a finer level of detail that shows additional compnonents and features of such a system.

In FIG. 2, steam condensate 201 is passed into a plurality of coolers 230 to allow for heat exchange between the steam condensate 201 and cooling water 231. The plurality of coolers 230 can be used, for example, to allow a first sample of steam condensate 201 to be cooled while a second sample is being acquired in a second cooler. Valves 239 can be used to control the flow of condensed steam 201 to the various coolers 230. After heat exchange, the heat exchanger water can be drained, such as for external cooling and then recycle as additional cooling water 231. The cooled steam condensate 291 can then be passed through valve 209. In FIG. 2, valve 209 corresponds to a three-way valve. This can allow the cooled condensed steam to be shunted to a common drain 297 when the sample chamber 210 is not available and/or ready. When it is desired to characterize the hydrocarbon content of a sample of cooled condensed steam 291, the three-way valve 209 can be opened to allow cooled condensed steam 291 to enter sample chamber 210. The excess water delivered to sample chamber 210 can leave sample chamber 210 via inner overflow tube 220 and exit via drain 227. After a period of time, three-way valve 209 can be closed, and any remaining water at or above the level of the top of inner overflow tube 220 can be drained 227. Valve 229 can then also be closed. After any optional purging of vapor chamber 240 with nitrogen 241, and/or optional reducing of pressure in vapor chamber 240 via vacuum line 281, valve 219 can be opened to allow transfer of gas from sample chamber 210 to vapor chamber 240. Optionally, an additional vent valve (not shown) can be tied in under valve 219. This additional valve can be beneficial in situations where it is desirable to completely empty the sample chamber 210. Prior to, during, or after opening of valve 219, sample chamber 210 and vapor chamber 240, and/or the fluids in sample chamber 210 and vapor chamber 240, can be heated to a desired temperature. The gas transferring from sample chamber 210 to vapor chamber 240 can also pass through a filter 244 to remove particles or droplets that may be entrained in the transfer gas flow. Valve 219 can then be closed. Optionally, vapor chamber 240 can then be pressurized using nitrogen 241. Valve 249 can then be opened to allow fluid communication between vapor chamber 240 and a detection volume (not explicitly shown) of gas chromatograph 260. In the aspect shown in FIG. 2, gas passing from vapor chamber 240 to the detection volume of gas chromatograph 260 can pass through a drying column 251 and a second filter 254. The drying column 251 can be used to reduce or minimize the water content of the gas that is passed into the gas chromatograph, while the second filter can reduce or minimize the content of particles and/or droplets in the flow that is passed into gas chromatograph 260.

Example of Process Flow for Pentane Detection

The following process flow provides an example of performing hydrocarbon detection in a condensed steam sample, such as pentane detection, using a system as described herein. This method of hydrocarbon detection can reduce or minimize maintenance requirements by eliminating the need for a conventional sparging system. This can avoid the difficulties with plugging that can be encountered when using a conventional sparging system with a steam stream that includes some types of contaminants.

To initiate detection of a hydrocarbon (such as pentane) in steam condensate, a stream of steam condensate can be passed into a cooling system and cooled to is cooled to a target temperature, such as a temperature in the range of 20°C. Cooling the steam condensate to a target temperature can allow for a substantially constant inlet temperature to the sample chamber between detection runs, which can facilitate performing comparisons between detection runs. Any convenient type of cooling system can be used, such as heat exchangers.

After cooling of the steam condensate, the cooled condensate can be sent to drain via a fast loop when not going to sample chamber which can assist with providing a representative sample when a new sample of condensed steam is desired. Diverting cooled condensate to drain can also reduce or minimize disruption of the condensate cooling and set flow (~0.5 l/min) when the sample in the sample chamber is being analyzed.

When it is desired to analyze a new sample of steam condensate, several actions can be performed to allow for analysis of the sample. Many of the actions can be performed in parallel, if desired. One action can be to evacuate the vapor chamber, such ~80 kPa-a). This can prepare the vapor chamber to receive a gas phase flow from the sample chamber. The isolation valve between the sample chamber and vapor chamber can be closed during this time, and can remain closed while the sample chamber is being flushed and/or drained.

Another action can be to heat the sample chamber (and optionally but preferably the vapor chamber) to a desired second temperature, such as 70° C. In some aspects, the sample chamber and/or vapor chamber can be substantially maintained at the desired second temperature. As fluids flow into the sample chamber and/or the vapor chamber, the fluids can begin to heat up toward the second temperature, and optionally may equilibrate to such temperature if sufficient time passes.

Still another action can be to flush the sample chamber with condensed steam. While flushing, the condensate enters the bottom of the chamber and overflows down a center overflow tube into the drain. After a sufficient flush period, the sample chamber can be allowed to drain. While draining, a vent (or vents) can be opened at the top of the sample chamber to prevent airlock while draining.

Once the inner tube is drained, the condensate remains at a known constant level in the annular space around the inner tube. An example of a suitable volume for the annular space in the sample chamber can be approximately 80 cm$^3$. After draining, the vent valve and the drain valve can be closed.

During or after draining, heating can be performed to increase the temperature of the water sample in the sample chamber. For example, this heating can be achieved by maintaining the sample chamber at a desired target temperature, such as 70° C. After flow to the sample chamber is stopped, and/or after draining has completed, the contents of the sample chamber can increase in temperature toward the temperature of the sample chamber. The water the sample chamber can then be held in the sample chamber for a desired period of time to allow for heating of the water. In other aspects, the heating can start after the draining is completed and the vent valve and drain valve have been closed. The desired heating time can correspond to any convenient heating time, such as a heating period of roughly 15 minutes. The heating time can allow the steam condensate in the sample chamber to reach a desired temperature, such as a temperature of >40° C..

After the heating time, the isolation valve between the sample chamber and vapor chamber can be opened (slowly) to equilibrate the sample chamber and the vapor chamber. Once equilibrated, the chamber pressure can be approximately atmospheric or slightly negative (relative to gauge). After equilibration, the isolation valve can be closed. The vapor chamber can then be pressurized to a desired pressure, such as a pressure of roughly 70 kpa-g. A suitable gas for pressurizing the chamber can be N2, but other convenient inert gases can also be used.

After the vapor chamber reaches the desired pressure, the valve between the vapor chamber and the gas chromatograph can be opened. This can send gas from the vapor chamber into the gas chromatograph through a Nafion dryer (or other suitable dryer) to remove residual moisture. The sample can then be analyzed using the gas chromatograph to determine a hydrocarbon content.

It is noted that the above method allows for target temperatures and pressures to be reached at various points in the method, along with equilibration at various points. By allowing for equilibration and/or by achieving target temperatures and pressure, variations between detection runs can be reduced or minimized. This can allow for comparison of values between runs. Additionally, this can allow condensed steam samples including known amounts of pentane to be pushed into the sample chamber to calibrate the system. This type of calibration can allow for quantitative determination of hydrocarbon contents (such as pentane contents) within a sample.

Examples of Pentane Detection

A sample chamber including an inner overflow tube and a vapor chamber were heated and maintained at 70° C. A valve was maintained in the closed position to isolate the sample chamber from the vapor chamber. The vapor chamber was evacuated to roughly 88 kPa-a using a venture. Condensed steam samples containing various amounts of $C_5$ alkane were pumped into the sample chamber. The $C_5$ alkane corresponded to a mixture of both n-pentane and isopentane. The condensed steam was at 20° C. prior to pumping into the sample chamber. After 2 minutes, the flow of condensed steam was stopped by closing a valve and excess water was allowed to drain via the inner overflow tube. The overflow tube was allowed to empty and then a valve associated with the overflow drain was closed.

The remaining water in the sample chamber was then held in the sample chamber for 15 minutes, to allow time for the water to reach a temperature of greater than ~40° C. The isolation valve between the vapor chamber and the sample chamber was then slowly opened to allow pentane evaporation into the vapor chamber. The vapor chamber pressure was equalized with the head space in the sample chamber. Evaporation of pentane and/or transfer into the vapor chamber was maintained for a period of time to allow equilibration of the pressure between the sample chamber and the vapor chamber. The isolation valve was then closed. A nitrogen flow was then used to pressurize the vapor chamber to ~170 kPa-a (~70 kPa-g). A valve was then opened to allow gas from the vapor chamber to pass into a gas chromatography unit for characterization. The gas chromatography unit included a thermal conductivity detector.

FIGS. 3, 4, 5, and 6 show results from the thermal conductivity detector from condensed steam samples containing 25 vppm, 50 vppm, 75 vppm, and 100 vppm of pentane, respectively. As shown in FIGS. 3-6, distinct peaks were visible in the thermal conductivity detector plots for n-pentane and isopentane. Because of the similarity in the way each sample was prepared, the quantitative differences in the amount of pentane in the condensed steam samples can be correlated with the area under the peaks in the thermal conductivity detector plots. While quantitative determination of hydrocarbon amounts may not always be necessary, such quantitative comparison can be beneficial for determining a rate at which the pentane content (or other hydrocarbon content) is increasing within a series of steam condensate samples.

Additional Embodiments

Embodiment 1. A method for characterizing hydrocarbon content in steam condensate, comprising: flowing water comprising condensed steam and at least one hydrocarbon at a first temperature through a sample chamber comprising an inner overflow tube, the inner overflow tube defining an annular volume between the inner overflow tube and an interior surface of the sample chamber; stopping the flow of water into the sample chamber; heating the sample chamber (during and/or after the stopping the flow of water) to a second temperature of 40° C. to 90° C.; transferring gas comprising the at least one hydrocarbon from the sample chamber into a vapor chamber; isolating the vapor chamber from the sample chamber; passing, after isolation, at least a portion of to the transferred gas from the vapor chamber into a detection volume; and characterizing a hydrocarbon content in the detection volume via gas chromatography, the flow of water optionally comprising condensed steam from a heat exchanger system.

Embodiment 2. A method for characterizing a content of a compound in steam condensate, comprising: flowing water comprising condensed steam and at least one compound having a boiling point less than 100° C. at 100 kPa-a (or less than 95° C.) at a first temperature through a sample chamber comprising an inner overflow tube, the inner overflow tube defining an annular volume between the inner overflow tube and an interior surface of the sample chamber; stopping the flow of water into the sample chamber; heating the sample chamber (during and/or after the stopping the flow of water) to a second temperature of 40° C. to 90° C.; transferring gas comprising the at least one hydrocarbon from the sample chamber into a vapor chamber; isolating the vapor chamber from the sample chamber; passing, after isolation, at least a portion of the transferred gas from the vapor chamber into a detection volume; and characterizing a hydrocarbon content in the detection volume via gas chromatography, the flow of water optionally comprising condensed steam from a heat exchanger system, the at least one compound optionally comprising at least one hydrocarbon-like compound.

Embodiment 3. The method of any of the above embodiments, the method further comprising draining water from the sample chamber via the inner overflow tube after stopping the flow of water into the sample chamber, the water level in the sample chamber optionally being at or above a top surface of the inner overflow tube prior to the stopping of the flow of water, the draining optionally further comprising opening a vent in the sample chamber during the draining.

Embodiment 4. The method of any of the above embodiments, wherein the sample chamber is heated to the second temperature prior to or during the flowing of water through the sample chamber; or wherein the vapor chamber is heated to the second temperature prior to or during the transferring of gas comprising the at least one hydrocarbon; or a combination thereof.

Embodiment 5. The method of any of the above embodiments, wherein characterizing the hydrocarbon content in the detection volume comprises determining an amount of hydrocarbon content using a thermal conductivity detector; or wherein characterizing the hydrocarbon content in the detection volume comprises comparing a thermal conductivity of the at least a portion of the transferred gas in the detection volume with a thermal conductivity of a reference flow in a reference volume.

Embodiment 6. The method of any of the above embodiments, wherein characterizing the hydrocarbon content in the detection volume comprises characterizing a pentane content in the detection volume.

Embodiment 7. The method of any of the above embodiments, wherein the at least one hydrocarbon comprises pentane, isopentane, or a combination thereof.

Embodiment 8. The method of any of the above embodiments, wherein the first temperature is 5° C. to 50° C., or 10° C. to 40° C., or 5° C. to 30° C.

Embodiment 9. The method of any of the above embodiments, wherein the second temperature is 50° C. to 70° C., or 60° C. to 80° C., or or 70° C. to 90° C.; or wherein the second temperature is greater than the first temperature by at least 10° C., or at least 20° C.; or a combination thereof.

Embodiment 10. The method of any of the above embodiments, wherein the sample chamber comprises a vertically-oriented sample chamber.

Embodiment 11. The method of any of the above embodiments, further comprising pressurizing the vapor chamber to a pressure of 50 kPa-g or more (or 70 kPa-g or more, or 90 kPa-g or more) after isolating the vapor chamber and prior to passing the at least a portion of the transferred gas into the detection volume, the pressurizing optionally comprising pressurizing with $N_2$.

Embodiment 12. A system for characterizing a hydrocarbon content in steam condensate, comprising: a sample chamber comprising a sample inlet, an overflow tube, an overflow tube outlet, and a sample outlet, the sample inlet being in selective fluid communication with a source of water comprising condensed steam, the sample chamber optionally further comprising a sample vent; a heater associated with the sample chamber; a vapor chamber in selective fluid communication with the sample outlet via at least a first valve; a detection volume in selective fluid communication with the vapor chamber via at least a second valve; and a gas chromatograph associated with the detection volume for characterizing a hydrocarbon content in the detection volume.

Embodiment 13. The system of Embodiment 12, wherein the gas chromatograph comprises a thermal conductivity detector associated with the detection volume; or wherein the detection volume comprises a chromatography column; or a combination thereof.

Embodiment 14. The system of Embodiment 12 or 13, the system further comprising a gas source in selective fluid communication with the vapor chamber via at least a third valve, the gas source optionally comprising a source of $N_2$.

Embodiment 15. The system of any of Embodiments 12 to 14, wherein the source of water comprising condensed steam comprises a source of water comprising condensed steam from a heat exchanger.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for characterizing hydrocarbon content in steam condensate, comprising:
    flowing water comprising condensed steam and at least one hydrocarbon at a first temperature through a sample chamber comprising an inner overflow tube, the inner overflow tube defining an annular volume between the inner overflow tube and an interior surface of the sample chamber;
    stopping the flow of water into the sample chamber;
    heating the sample chamber to a second temperature of 40° C. to 90° C.;
    transferring gas comprising the at least one hydrocarbon from the sample chamber into a vapor chamber;
    isolating the vapor chamber from the sample chamber;
    pressurizing the vapor chamber to a pressure of 50 kPa-g or more after isolating the vapor chamber;
    passing, after isolation, at least a portion of the transferred gas from the vapor chamber into a detection volume; and
    characterizing a hydrocarbon content in the detection volume via gas chromatography.

2. The method of claim 1, the method further comprising draining water from the sample chamber via the inner overflow tube after stopping the flow of water into the sample chamber.

3. The method of claim 2, wherein a water level in the sample chamber is at or above a top surface of the inner overflow tube prior to the stopping of the flow of water.

4. The method of claim 2, wherein draining water from the chamber further comprises opening a vent in the sample chamber during the draining.

5. The method of claim 1, wherein the sample chamber is heated to the second temperature prior to or during the flowing of water through the sample chamber.

6. The method of claim 1, wherein characterizing the hydrocarbon content in the detection volume comprises determining an amount of hydrocarbon content using a thermal conductivity detector.

7. The method of claim 1, wherein characterizing the hydrocarbon content in the detection volume comprises comparing a thermal conductivity of the at least a portion of the transferred gas in the detection volume with a thermal conductivity of a reference flow in a reference volume.

8. The method of claim 1, wherein characterizing the hydrocarbon content in the detection volume comprises characterizing a pentane content in the detection volume.

9. The method of claim 1, wherein the at least one hydrocarbon comprises pentane, isopentane, or a combination thereof.

10. The method of claim 1, wherein the first temperature is 5° C. to 50° C.

11. The method of claim 1, wherein the second temperature is 60° C. to 80° C.; or wherein the second temperature is greater than the first temperature by at least 10° C., or at least 20° C.; or a combination thereof.

12. The method of claim 1, wherein the flow of water comprises a flow of condensed steam from a heat exchanger system.

13. The method of claim 1, wherein the sample chamber comprises a vertically-oriented sample chamber.

14. The method of claim 1, wherein the vapor chamber is pressurized with $N_2$.

* * * * *